United States Patent
Ko et al.

(10) Patent No.: US 10,493,126 B2
(45) Date of Patent: *Dec. 3, 2019

(54) COMBINATION THERAPY FOR AMELIORATING ADVERSE SIDE EFFECTS CAUSED BY CHEMOTHERAPY

(71) Applicant: YEASTERN BIOTECH CO., LTD, Taipei (TW)

(72) Inventors: Jiunn-Liang Ko, Taichung (TW); Ting-Yi Hou, Taichung (TW); Ming-Fang Wu, Taichung (TW); Tzu-Chih Chen, Taipei (TW)

(73) Assignee: YEASTERN BIOTECH CO., LTD., Taipei (TW)

( * ) Notice: Subject to any disclaimer, the term of this patent is extended or adjusted under 35 U.S.C. 154(b) by 148 days.

This patent is subject to a terminal disclaimer.

(21) Appl. No.: 15/125,167

(22) PCT Filed: Mar. 12, 2015

(86) PCT No.: PCT/CN2015/074059
§ 371 (c)(1),
(2) Date: Sep. 11, 2016

(87) PCT Pub. No.: WO2015/135483
PCT Pub. Date: Sep. 17, 2015

(65) Prior Publication Data
US 2017/0173110 A1 Jun. 22, 2017

Related U.S. Application Data

(60) Provisional application No. 61/952,311, filed on Mar. 13, 2014.

(51) Int. Cl.
| | |
|---|---|
| A61K 38/16 | (2006.01) |
| A61K 31/337 | (2006.01) |
| A61K 36/06 | (2006.01) |
| A61K 45/06 | (2006.01) |
| A61K 31/555 | (2006.01) |
| A61K 33/24 | (2019.01) |
| A61K 9/00 | (2006.01) |

(52) U.S. Cl.
CPC .......... *A61K 38/168* (2013.01); *A61K 9/0053* (2013.01); *A61K 31/337* (2013.01); *A61K 31/555* (2013.01); *A61K 33/24* (2013.01); *A61K 36/06* (2013.01); *A61K 45/06* (2013.01)

(58) Field of Classification Search
None
See application file for complete search history.

(56) References Cited

U.S. PATENT DOCUMENTS

| | | |
|---|---|---|
| 7,531,627 B2 | 5/2009 | Chien |
| 8,163,519 B2 | 4/2012 | Ko |
| 8,629,096 B2 | 1/2014 | Ko |
| 2005/0196409 A1* | 9/2005 | Dao ...................... A61K 36/074 424/195.15 |
| 2007/0071766 A1* | 3/2007 | Ko .......................... A61K 38/16 424/185.1 |
| 2009/0042776 A1 | 2/2009 | Ko |
| 2011/0009597 A1 | 1/2011 | Sun |

FOREIGN PATENT DOCUMENTS

| | | |
|---|---|---|
| EP | 3034515 | 6/2016 |
| TW | 201206457 A1 | 2/2012 |

OTHER PUBLICATIONS

Chen et. al, In vivo Anti-candidal Activity Induced by a Traditional Chinese Herbal Medicine, Ganoderma lucidum, Jpn. J. Med. Mycol. vol. 33, 505-512, 1992.
Lin et. al, Evaluation of the anti-inflammatory and liver-protective effects of Anoectochilus formosanus, Ganoderma lucidum and Gynostemma pentaphyllun in rats, American Journal of Chinese Medicine, vol. XXI, No. 1, pp. 59-69.
Hornet et. al, Basidiomycete allergens: comparison of three *Ganoderma* species, Allergy 1993: 48: 110-116.
Kino et. al, Isolation and Characterization of a New Immunomodulatory Protein, Ling Zhi-8 (LZ-8), from Ganoderm lucidium, vol. 264, No. 1, Issue of Jan. 5, pp. 472-478, 1989.
Kawagishi et al., 5'-Deoxy-5'-Methylsulphinyladenosine, a platelet aggregation inhibitor from Ganoderma lucidum, Phytochemistry, vol. 32, No. 2, pp. 239-241, 1993.
Ko et al., A new fungal immunomodulatory protein FIP-fve isolated from the edible mushroom, *Flammulina velutines* and its complete amino acid sequence, Eur. J. Biochem, 228, 244-249 (1995).
Van Der Hem, Ling ZHI-8: Studies of a New Immunomodulating Agent, vol. 60, 438-443, No. 5, Sep. 16, 1995.
Hsu et al., Fip-vvo, a new fungal immunomodulatory protein isolated from Volvariella volvacea, Biochem. J. (1997) 323, 557±565.
Kong et al., High-Yield Production in *Escherichia coli* of Fungal Immunomodulatory Protein Isolated from Flammulina velutipes and Its Bioactivity Assay in Vivo, Int. J. Mol. Sci. 2013, 14, 2230-2241; doi:10.3390/ijms14022230.
Han et al., Heterologous expression of the immunomodulatory protein gene from Ganoderma sinense in the basidiomycete Coprinopsis cinerea, Journal of Applied Microbiology 109, 1838-1844, 2010.
Wang et al., Fungal immunomodulatory protein from Flammulina velutipes induces Interferon—Production through p38 Mitogen-activated protein kinase signaling pathway, J. Agric. Food Chem. 2004, 52, 2721-2725, 2004.

(Continued)

*Primary Examiner* — Brian Gangle
(74) *Attorney, Agent, or Firm* — Hannah Tien

(57) ABSTRACT

The invention generally relates to an immunomodulatory protein and a chemotherapeutic agent for simultaneous, contemporaneous or sequential use in the treatment of diseases, more particularly of proliferative diseases, still more particularly of cancer(s), to a combination of an FIP and a chemotherapeutic agent, as well as to the medical and biotechnological applications thereof, more particularly in the field of the treatment of diseases, more particularly of proliferative diseases, still more particularly of cancer(s).

9 Claims, 5 Drawing Sheets
Specification includes a Sequence Listing.

(56) References Cited

OTHER PUBLICATIONS

Lin et al., Dimerization of the N-terminal Amphipathic a-Helix Domain of the Fungal Immunomodulatory Protein from Ganoderma tsugae (Fip-gts) Defined by a Yeast Two-hybrid System and Site-directed Mutagenesis, vol. 272, No. 32, Issue of Aug. 8, pp. 20044-20048, 1997.
Wang et al., Immunomodulatory Effects of Fungal Proteins, Current Topics in Nutraceutical Research vol. 10, No. 1, pp. 1-12, 2012.
Li et al., Recent status and prospects of the fungal immunomodulatory protein family, Critical Reviews in Biotechnology, 2011; 31(4): 365-375, 2011.
Oken et al., Toxicity and response criteria of the eastern cooperative oncology group, Am J. Clin Oncol (CCT) 5: 649-655, 1982.

* cited by examiner

COMBINATION THERAPY FOR AMELIORATING ADVERSE SIDE EFFECTS CAUSED BY CHEMOTHERAPY

CROSS-REFERENCES

THIS APPLICATION CLAIMS PRIORITY TO U.S. PATENT APPLICATION NO. 61/952,311 FILED Mar. 13, 2014, THE ENTIRETY OF WHICH IS INCORPORATED HEREIN BY REFERENCE. This application contains a Sequence Listing in computer readable form. The computer readable form is incorporated herein by reference.

FIELD OF THE INVENTION

The invention relates to a fungal immunomodulatory protein (FIP) and a chemotherapeutic agent for simultaneous, contemporaneous or sequential use in the treatment of diseases, more particularly of proliferative diseases, still more particularly of cancer(s), to a combination of an FIP and a chemotherapeutic agent, as well as to the medical and biotechnological applications thereof, more particularly in the field of the treatment of diseases, more particularly of proliferative diseases, still more particularly of cancer(s). The invention further relates to methods and compositions for protecting a subject from an adverse side effect caused by chemotherapeutic treatment of diseases, more particularly of proliferative diseases, still more particularly of cancer(s).

DESCRIPTION OF THE RELATED ART

*Ganoderma* is a rare and valuable herb in Chinese medicine. It has been known in China for over 5,000 years as "Ling Zhi". There are a variety of Ganodermas, including *G. lucidum* (red), *G. applanatum* (brown), *G. tsugae* (red), *G. sinense* (black), and *G. oregonense* (dark brown).

It has been known that Ling Zhi has anti-allergy (Chen H. Y et al., *J. Med. Mycol.* 1992; 33:505-512), hepatoprotective (Lin J. M. et al., *Am J Chin Med.* 1993; 21(1):59-69) and anti-tumor effects (Wasser S P, *Crit. Rev Immunol* 1999. 19:65-96) and immune advantages (Kino, *J. Biol. Chem.* 1989. 264(1): 472-8). However, Ling Zhi is used restrictedly in the form of extract of raw material (Horner W. E. et al., *Allergy* 1993; 48:110-116) or small molecules (Kawagishi H., et al., *Phytochemistry* 1993; 32: 239-241).

Several proteins from edible fungi such as *Ganoderma Lucidium* (Ling zhi or Reishi), *Volvariella Volvacea* (Chinese Mushroom), *Flammulina Velutipes* (Golden needle mushroom) share similar amino acid sequences and immunomodulatory functions. These proteins were named fungal immunomodulatory proteins (FIPs) (Ko J. L., *Eur. J. Biochem.* 1995; 228:244-249).

In 1989 Kino et al. found protein Ling Zhi-8 in *G. lucidum* (Kino K. et al., *J. Biol. Chem.* 1989; 264(1): 472-8). LZ-8 has positive effects on systemic anaphylaxis, and has been used for the treatment of liver cancer and preventing diabetes. LZ-8 and another immunomodulatory protein, FIP-fve, obtained from *Flammulina Velutipes*, have amino acid sequences and folding structures similar to the heavy chain of immunoglobulin. Further, it has been shown that by enhancing the expression of LZ-8, these proteins show immunomodulatory activities and have positive effects on patients with systemic anaphylaxis (Ko J. L., *Eur. J. Biochem.* 1995; 228:244-249). It was further discovered that FIP can activate human peripheral blood mononuclear cells (HPBMCs), enhance the proliferation of HPBMCs and mouse splenocyte (van der Hem, et al., Transplantation, 1995. 60, 438-443.). Using $^3$H-thymidine to measure the effect of FIP-gts on proliferation, it was further discovered that compared to PHA (phytoagglutinin), 5 µg/ml of FIP-gts or 100 µg/ml FIP-fve is sufficient to reach the maximum proliferation of human lymphocytes (Hsu, C., cited supra). Concerning non-B and non-T cells, it was found that FIP-gts could only promote the proliferation of Non-B cells.

Similar to PHA and other lectin mitogens, LZ-8 is mitogenic. LZ-8 primarily proliferates T cells with the help of monocyte. A new family of fungal immunomodulatory proteins (FIPs) (Ko J L, et al., *Eur J Biochem* 1995; 228(2):244-249.) has recently been identified. At least ten FIPs have been identified and isolated from *Ganoderma lucidum*, *Flammulina veltipes*, *Volvariella volvacea*, *Ganoderma tsugae*, *Ganoderma japoncium*, *Ganoderma microsporum*, *Ganoderma sinense* and *Nectria haematococca*, *Tremella fuciformis*, *Antrodia camphorate* and designated LZ-8 (also known as FIP-glu), FIP-fve, FIP-vvo, FIP-gts, FIP-gja (GenBank: AY987805), FIP-gmi, FIP-gsi, FIP-nha, FIP-tfu (GenBank: EF152774) and FIP-aca, respectively (Hsu H C, et al., *Biochem J* 1997; 323 (Pt 2):557-565; Kong et al., *Int. J. Mol. Sci.* 2013; 14: 2230-2241; Han et al., *J Appl Microbiol* 2010, 109:1838-44; U.S. Pat. No. 7,531,627; and China Patent No. CN102241751B). FIPs are mitogenic in vitro for human peripheral blood lymphocytes (hPBLs) and mouse splenocytes. They induce a bell-shaped dose-responsive curve similar to that of lectin mitogens. Activation of hPBLs with FIPs results in the increased production of molecules of IL-2, IFN-γ and tumor necrosis factor-α associated with ICAM-1 expression (Wang P H, et al., *J Agric Food Chem* 2004; 52(9):2721-2725.). FIPs can also act as immunosuppressive agents. In vivo these proteins can prevent systemic anaphylactic reactions and significantly decrease footpad edema during Arthus reaction in mouse. These observations suggest that FIPs are both health promoting and therapeutic.

Lin et al. have purified an immunomodulatory protein from the mycelium of *Ganoderma tsugae*, named FIP-gts (Lin, W. H., et al., *J Biol. Chem.* 1997. 272, 20044-20048.). The FIP-gts found in the fruit body of *Ganoderma tsugae* has no immunomodulatory effect; only the protein found in the mycelium has the effect. After cloning, the DNA sequence of FIP-gts was found to be identical to the sequence of LZ-8 in *Ganoderma lucidium*. Both proteins exhibited the same immunoactivity, demonstrating that they are the same protein.

Analyzing the secondary structure with Garnier analysis, FIP-gts was predicted to have two α-helices, seven β-sheets and one β-turn. The molecular weight of FIP-gts was determined to be 13 kD using SDS-PAGE analysis. Connecting the amino acids with 20 µM glutaraldegyde (protein conjugate), FIP-gts was found to form a 26 kD homodimer.

In addition, three fungal proteins were found by Blast-formation stimulatory activity assay (BFSA). Except proteins found in *Ganoderma lucidium*, blood clotting proteins found in *Flammulina velutipes* and *Volvariella volvacea* have partial immunomodulate activity. Their molecular weights were around 13 kD, and neither of them contains histidine, cysteine or methionine. They are a kind of lectins that are linked to carbohydrates.

Although the immunomodulatory activity of FIPs has been studied extensively, their anticancer functions have not been investigated until recent years. U.S. Pat. No. 8,163,519 assigned to the Applicant teaches that LZ-8 was found useful for treating liver cancer in the previous study. U.S. Pat. No. 8,629,096, also assigned to the Applicant, discloses that LZ-8 can potently inhibit the proliferation and invasion of tumor cells, both in vitro and in vivo, suggesting the potential utility of the FIPs as a broad-spectrum anticancer agent. U.S. Patent Publication No. 2011/009597 provides additional experimental data showing the capability of a recombinant LZ-8 protein expressed from *Pichia* yeast in inducing the programmed cell death of leukemia cells in vitro and suppressing the growth of hepatoma cells in vivo.

Chemotherapy is the treatment of cancer with one or more chemotherapeutic agents, normally anti-neoplastic drugs, as part of a standardized regimen. Chemotherapy may be given with a curative intent or it may aim to prolong life or to palliate symptoms. It is often used in conjunction with other cancer treatments, such as radiation therapy, surgery, and/or hyperthermia therapy. Certain chemotherapeutic agents also have a role in the treatment of other conditions, including ankylosing spondylitis, multiple sclerosis, Crohn's disease, psoriasis, psoriatic arthritis, systemic lupus erythematosus, rheumatoid arthritis, and scleroderma.

Chemotherapy is known to come with a long list of adverse side effects—from debilitating nausea and hair loss to extreme fatigue. Most of the common chemotherapeutic medications affect mainly the fast-dividing cells of the body, such as blood cells and the cells lining the mouth, stomach, and intestines. Chemotherapy-related side effects can occur acutely after administration, within hours or days, or chronically, from weeks to years.

Thus, there is a need for new therapeutic combinations and methods that provide protection to patients against adverse side effects caused by chemotherapy.

SUMMARY OF THE INVENTION

In the first aspect provided herein is a method for protecting a subject from an adverse side effect caused by chemotherapeutic treatment, comprising administering to said subject an effective amount of a fungal immunomodulatory protein (FIP) sufficient to ameliorate the adverse side effect.

In the second aspect provided herein is a pharmaceutical composition for protecting a subject from an adverse side effect caused by chemotherapeutic treatment, comprising an effective amount of a fungal immunomodulatory protein (FIP) sufficient to ameliorate the adverse side effect.

In the third aspect provided herein is use of a fungal immunomodulatory protein in manufacturing a medicament for protecting a subject from an adverse side effect caused by a chemotherapeutic agent.

In the fourth aspect provided herein is a fungal immunomodulatory protein for use in protecting a subject from an adverse side effect caused by chemotherapeutic treatment, wherein the FIP is in an effective amount sufficient to ameliorate the adverse side effect.

In the fifth aspect provided herein is a combination comprising a chemotherapeutic agent and a fungal immunomodulatory protein (FIP), particularly a combination comprising a chemotherapeutic agent and an effective amount of a FIP sufficient to ameliorate the adverse side effect caused by the chemotherapeutic agent, for simultaneous, contemporaneous or sequential use in the treatment of a proliferative disease in a subject.

In the sixth aspect provided herein is a method for treating a proliferative disease in a subject in need of such treatment, comprising administering to the subject a chemotherapeutic agent in combination with a fungal immunomodulatory protein (FIP), particularly a chemotherapeutic agent in combination with an effective amount of a FIP sufficient to ameliorate the adverse side effect caused by the chemotherapeutic agent.

In the seventh aspect provided herein is use of a combination in manufacturing a medicament for treating a proliferative disease in a subject in need of such treatment, wherein the combination comprises a chemotherapeutic agent and an effective amount of a FIP sufficient to ameliorate the adverse side effect caused by the chemotherapeutic agent.

BRIEF DESCRIPTION OF THE DRAWINGS

The above and other objects, features and effects of the invention will become apparent with reference to the following description of the preferred embodiments taken in conjunction with the accompanying drawings, in which.

DETAILED DESCRIPTION OF THE INVENTION

Figure 1:
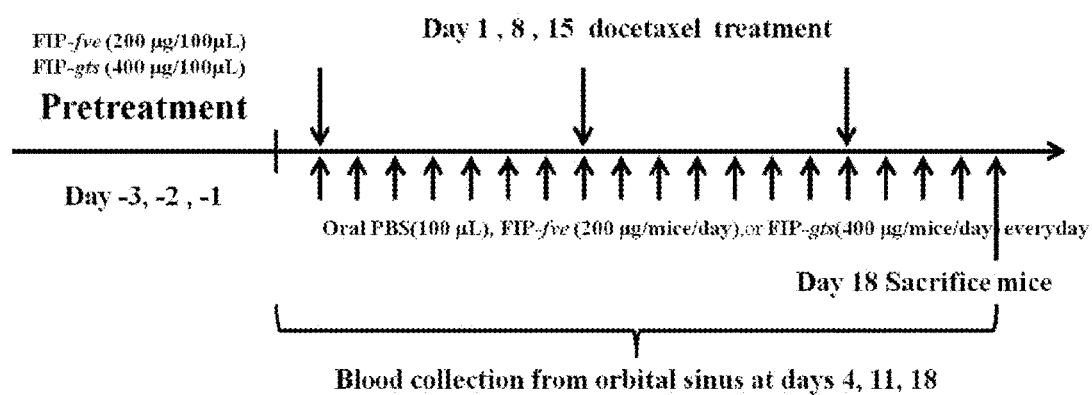
FIG. 1 shows the protocol used for the mice model of pre-treatment with PBS, FIP-fve or FIP-gts, followed by co-treatment with Docetaxel.

As used herein, the singular forms "a," "an," and "the" include plural referents unless the content clearly dictates otherwise. Thus, for example, reference to a composition containing "a chemotherapeutic agent" may mean that the composition includes a mixture of two or more chemotherapeutic agents. It should also be noted that the term "or" is generally employed in its sense including "and/or" unless the content clearly dictates otherwise.

The term "fungal immunomodulatory protein," or abbreviated as "FIP," is used herein to refer to a protein belonging to the protein family first defined in Ko et al., *Eur. J. Biochem.* 1995; 228:244-249, based on the similarity in amino acid sequence and the effects on immunological response. It has been reported that the immunomodulatory proteins in the FIP family share a sequence homology of at least 57%. In particular, the primary structures of FIP-gts, FIP-fve, FIP-vvo and LZ-8 exhibit a sequence homology of 60-70% (Kong et al., *Int. J. Mol. Sci.* 2013, 14, 2230-2241; China Patent No. CN102241751B; Wang X F et al., *Curr. Topics Nutraceutical Res.* 2012, 10(1): 1-12; and Li O Z et al., *Crit. Rev. Biotech.* 2011, 31(4):365-375). Therefore, the term "fungal immunomodulatory protein" used herein is intended to encompass any polypeptide having an amino acid homology of at least 57%, preferably at least 60%, at least 70%, at least 80%, at least 90% or at least 95%, to the amino acid sequence of FIP-gts indicated by SEQ ID NO: 1 and having the ability to induce, enhance or extend the immune response in a subject. In one preferred embodiment, the fungal immunomodulatory protein has an amino acid sequence selected from the group consisting of SEQ ID NO: 1 (FIP-gts), SEQ ID NO: 2 (FIP-fve), SEQ ID NO: 3 (FIP-vvo), SEQ ID NO: 4 (LZ-8), SEQ ID NO: 5 (FIP-gja), SEQ ID NO: 6 (FIP-gmi), SEQ ID NO: 7 (FIP-gsi) and SEQ ID NO: 8 (FIP-nha), and functional variants thereof as an immunomodulatory agent. In another preferred embodiment, the FIP is derived from a *Ganoderma* species or *Volvariella volvacea* and, more preferably, has an amino acid sequence selected from the group consisting of SEQ ID NO: 1, SEQ ID NO: 2, SEQ ID NO: 3, SEQ ID NO: 4, SEQ ID NO: 5, SEQ ID NO: 6 and SEQ ID NO: 7. The most preferred is that comprising, consisting essentially of, or consisting of an amino acid sequence of SEQ ID NO: 1.

The FIP used herein may be obtained from a natural source, from a fungal culture or by recombinant expression in a prokaryotic or eukaryotic microorganism host, such as a bacterium or yeast host. The FIP thus obtained may be either in the form of a crude preparation or in a refined formulation separated, fractionated, or partially or substantially purified from the fungal matter by any suitable technique. Preferably, the protein is at least partially purified before use. A useful process for preparing the FIP is disclosed in WO2005040375A1, which involves culturing a yeast transformant harboring an expression vector carrying an FIP gene and harvesting a recombinant FIP protein from the yeast culture. Other useful methods may be found from, for example, Kong et al. (supra) and CN101205553A; and Wang X F et al., *Curr. Topics Nutraceutical Res.* 2012; 10(1): 1-12.

In the case where the FIP used is LZ-8 or FIP-gts, it can be either isolated directly from *G. lucidum* or *G. tsugae*, or prepared by recombinant protein technology in a host cell system. The host cells may be a yeast or bacterium system. Preferably, said host cell system is selected from the group consisting of *Saccharomyces cerevisiae*, *Pichia pastoris*, *Hansenula polymorpha*, *Candida utilis*, *Candida boidinii*, *Candida maltosa*, *Kluyveromyces lactis*, *Yarrowia lipolytica*, *Schwanniomyces occidentalis*, *Schizosaccharomyces pombe*, *Torulopsis* sp., *Arxula adeninivorans*, *Aspergillus* sp. (such as *A. nidulans*, *A. niger*, *A. awamori*, and *A. oryzae*), and *Tricoderma* sp. (such as *T. reesei*).

The term "chemotherapeutic agent" is used herein in its broadest sense to include any chemical compound or drug with anti-cell proliferation activity that inhibits or halts the growth of cancerous cells or immature pre-cancerous cells, kills cancerous cells or immature pre-cancerous cells, increases the susceptibility of cancerous or pre-cancerous cells to other chemotherapeutic agents, and/or inhibits metastasis of cancerous cells. For example, a chemotherapeutic agent may include, but is not limited to, any agent that interferes with cell division, disrupts normal functionality of microtubules, inhibits utilization of a metabolite, substitutes nucleotide analogs into cellular DNA, or inhibits enzymes necessary for DNA replication.

In some preferred embodiments, the chemotherapeutic agent is useful for the treatment of proliferative diseases, including a solid tumor disease, such as breast cancer, cancer of the colon and generally the GI tract including gastric cancer, hepatoma; lung cancer, in particular small-cell lung cancer and non-small-cell lung cancer, renal cancer, mesothelioma, glioma, squamous cell carcinoma of the skin, head and neck cancer, genitourinary cancer, e.g., cervical, uterine, ovarian, testicles, prostate or bladder cancer; Hodgkin's disease, carcinoid syndrome, Kaposi's sarcoma, Paget's disease of bone, tumor-induced hypercalcaemia, bone metastasis and multiple myeloma and a liquid tumor, e.g., leukemia. The chemotherapeutic agent is also suitable to treat or prevent the metastatic spread of tumor and the growth or development of micrometastases.

Suitable classes of chemotherapeutic agents include (a) alkylating agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dicarbazine), (b) antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) natural products, such as vinca alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and (d) miscellaneous agents, such as platinum coordination complexes (e.g., cisplatin, carboplatin), substituted ureas (e.g., hydroxyurea), methylhydiazine derivatives (e.g., procarbazine), and adreocortical suppressants (e.g., mitotane), and mitotic inhibitors (e.g., taxanes).

In preferred embodiments, the chemotherapeutic agent is a mitotic inhibitor such as a microtubule stabilizing agent, a microtubule destabilizing agents and a microtubule polymerization inhibitor. These agents include, but are not limited to, taxanes, e.g., Paclitaxel and Docetaxel, vinca alkaloids, e.g., vinblastine, especially vinblastine sulfate, vincristine, especially vincristine sulfate, and vinorelbine and discodermolide, colchicines and epothilones and derivatives thereof, e.g., epothilone B or derivatives thereof. Among them, taxanes are particularly suitable for the purpose of the invention.

As used herein, the term "taxane" refers to a taxanes, taxines, and taxoids, as well as derivatives or analogs thereof. In some embodiments, the taxane includes, for example, Paclitaxel (trade name: Taxol®, Bristol-Myers Squibb), Docetaxel (trade name: Taxotere®, Aventis Pharmaceuticals); spicatin; taxane-2,13-dione, 5β,9β,10β-trihydroxy-, cyclic 9,10-acetal with acetone, acetate; taxane-2, 13-dione, 5β,9β,10β-trihydroxy-, cyclic 9,10-acetal with acetone; taxane-2β,5β,9β,10β-tetrol, cyclic 9,10-acetal with acetone; taxane; cephalomannine-7-xyloside; 7-epi-10-deacetylcephalomannine; 10-deacetylcephalomannine; cephalomannine; taxol B; 13-(2',3'-dihydroxy-3phenylpropionyl)baccatin III; yunnanxol; 7-(4-azidobenzoyl)baccatin III; N-debenzoyltaxol A; O-acetylbaccatin IV; 7-(triethylsilyl)baccatin III; 7,10-di-O-[(2,2,2,-trichloroethoxy)carbonyl]baccatin III; baccatin III 13-O-acetate; baccatin diacetate; baccatin; baccatin VII; baccatin VI; baccatin IV; 7-epi-baccatin III; baccatin V; baccatin I; baccatin III; baccatin A; 10-deactyl-7-epitaxol; epitaxol; 10-deacetyltaxol C; 7-xylosyl-10-deacetyltaxol; 10-deacetyltaxol-7-xyloside; 7-epi-10-deacetyltaxol; 10-deactyltaxol; or 10-deactyltaxol B.

In more preferred embodiments, the taxane is selected from the group consisting of Paclitaxel or Docetaxel. The most preferred is Docetaxel. As used herein, the term "Docetaxel" refers to (2R,3S)-N-carboxy-3-phenylisoserine, N-tert-butyl ester, 13-ester with 5, 20-epoxy-1,2, 4, 7, 10, 13-hexahydroxytax-11-en-9-one 4-acetate 2-benzoate, trihydrate. (CAS number: 114977-28-5) available under a generic name or under the trade name Taxotere®. The term "Paclitaxel" as used herein refers to the drug commercially available as generic or Taxol® and has an IUPAC name of (2α,4α,5β,7β,10β,13α)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate. The terms "Docetaxel" and "Paclitaxel" are also intended to include both naturally derived and related forms and chemically synthesized compounds or derivatives thereof with antineoplastic property.

Docetaxel and Paclitaxel are common prescription treatments for patients suffering from breast, prostate, ovarian, stomach, head and neck, and non-small-cell lung cancers. The two drugs share a similar pharmacological mechanism of action as mitotic inhibitors, where Docetaxel induces mainly the S-phase cell cycle arrest and Paclitaxel has primary actions in G2-M phase of the cell cycle.

For the purposes of the invention, the term "chemotherapeutic treatment" or "chemotherapy" refers to treatment of a subject with a chemotherapeutic agent defined above, such as chemotherapy treatments for a proliferative disease, e.g., cancer. In this context, the term "adverse side effect" or "adverse side effect caused by a chemotherapeutic agent" refers to any undesired consequence other than the desired effects for which the chemotherapeutic agent is intended, including any abnormality, defect, mutation, lesion, degeneration or injury which may be caused by taking the chemotherapeutic agent.

Typically, chemotherapeutic agents act by killing cells that divide rapidly, one of the main properties of most cancer cells. In this context, chemotherapy would also harm healthy cells that divide rapidly under normal circumstances, including cells in bone marrow, digestive tract and hair follicles, thus resulting in the adverse side effects. Therefore, the "adverse side effect" is intended to encompass myelosuppression (decreased production of blood cells, hence also immunosuppression and anemia), mucositis (inflammation of the lining of the digestive tract, causing nausea, vomiting, mouth soreness, anorexia and difficulty in swallowing), osteoporosis, fatigue, diminished quality of life, alopecia (hair loss) and pain. In one embodiment, the "adverse side effect" includes, but is not limited to, haematological disorders, such as pancytopenia, neutropenia, leucopenia, agranulocytosis, anaemia, febrile neutropenia and thrombocytopenia; digestive tract disorders, such as oral and gastrointestinal mucositis, nausea, vomiting, diarrhea, anorexia, mouth soreness and difficulty in swallowing; osteoporosis; diminished quality of life, asthenia and cancer-related fatigue; neurological disorders, such as neurosensory dysfunction and neuromotor dysfunction; alopecia; skin rash or itching; hypersensitive reactions; fluid retention; and lowered resistance to infections. In a more preferred embodiment, the "adverse side effect" is selected from the group consisting of leucopenia, anaemia, thrombocytopenia, gastrointestinal mucositis, chemotherapy-induced osteoporosis, diminished quality of life and cancer-related fatigue.

For assessment of the adverse side effects caused by chemotherapy, the inventors established a mice model in which the adverse side effects were induced by administering a representative chemotherapeutic agent. According to the disclosure provided herein, Docetaxel was selected as the representative chemotherapeutic agent, as the potential adverse side effects induced thereby are common to all chemotherapy and many of them have been documented. Docetaxel is a cell cycle specific agent used mainly for the treatment of breast, ovarian, prostate and non-small cell lung cancer, which acts by binding to cellular β-tubulin, increasing its polymerization and promoting microtubule assembly. The drug-tubulin binding inhibits tubulin depolymerization, causing the cells to be arrested in the S-phase of the cell cycle. Therefore, it is cytotoxic to all dividing cells in the body. As shown in Examples 1-4 below, typical adverse side effects, including myelosuppression, mucositis and osteoporosis, were induced in the mice model by administering Docetaxel.

FIP-gts and FIP-fve were chosen as representative of the FIP defined above. The inventors surprisingly found that the adverse side effects caused by chemotherapy in the mice model, preferably using the representative chemotherapeutic agent Docetaxel, were advantageously ameliorated by pre-administration and co-administration of the FIP.

The term "protecting a subject from an adverse side effect" as used herein may encompass preventing the adverse side effect from occurring in the subject and/or treating the adverse side effect after its emergence in the subject. In this regard, the term "preventing" includes reducing the severity/intensity of, or initiation of, the adverse side effect. The term "treating" includes alleviation of the adverse side effect after the emergence of the side effect. Nevertheless, the term "protecting" shall not be understood in the sense that there is always a 100% protection against the adverse side effect. Therefore, the term "ameliorate the adverse side effect" refers to a substantial lessening or extinguishing of the adverse side effect which has occurred or may occur in the subject.

The term "pre-administration" refers to administration of an FIP to a subject before the administration of a chemotherapeutic agent. In certain embodiments, the subject is given the FIP for a sufficient period of time, such as for a few days, weeks or months beforehand, prior to the administration of the chemotherapeutic agent, so as to allow the FIP to exert its effect on prevention of the adverse side effect. The term "co-administration" refers to administration of the two substances to a subject together or within a certain desired period of time.

In one embodiment, the adverse side effect induced by the Docetaxel-based chemotherapy is myelosuppression characterized by the reduced production of blood cells. Preferably, the degree of myelosuppression is evaluated by performing a standard complete blood count (CBC) to obtain whole blood profiles. As shown in Example 2 below, the myelosuppression, such as leucopenia, anaemia and thrombocytopenia, induced by Docetaxel was ameliorated by both FIP-gts and FIP-fve, particularly in terms of the restored levels of white blood cells, platelets and hemoglobin.

In another embodiment, the adverse side effect induced by chemotherapy is mucositis characterized by mucosal damage, such as a decrease in villi height which can be observed under microscope. As shown in Example 3 below, the mucositis, such as gastrointestinal mucositis, induced by Docetaxel was ameliorated by both FIP-gts and FIP-fve, particularly in terms of the restored structural integrity of intestinal villi in the mice model.

In still another embodiment, the adverse side effect induced by chemotherapy is osteoporosis characterized by osteopenia, such as decrease in bone density and loss of trabecular bone. For the purpose of the invention, the degree of osteoporosis is further evaluated in view of the structural integrity and adipogenesis of trabecular bone. As shown in Example 4 below, the osteoporosis induced by Docetaxel was ameliorated by both FIP-gts and FIP-fve, particularly in terms of the structural integrity and adipogenesis degree of trabecular bone in the mice model.

The inventors further conducted a clinical study on diminished quality of life (QOL) and cancer-related fatigue (CRF) caused by chemotherapy. The QOL and CRF of selected human patients were evaluated by the Eastern Cooperative Oncology Group (ECOG) Performance Status Scale from 0 to 5 (Oken M. M., et al., *Am. J. Clin. Oncol.;* 1982, 5(6): 649-55), where each grade represents:

0—Asymptomatic (Fully active, able to carry on all pre-disease activities without restriction);

1—Symptomatic but completely ambulatory (Restricted in physically strenuous activity but ambulatory and able to carry out work of a light or sedentary nature. For example, light housework, office work);

2—Symptomatic, <50% in bed during the day (Ambulatory and capable of all self care but unable to carry out any work activities. Up and about more than 50% of waking hours);

3—Symptomatic, >50% in bed, but not bedbound (Capable of only limited self-care, confined to bed or chair 50% or more of waking hours);

4—Bedbound (Completely disabled. Cannot carry on any self-care. Totally confined to bed or chair); and 5—Death.

It is known that cancer patients who undergo chemotherapy, such as those who received Docetaxel and/or cisplatin due to lung cancer, are confronted with a variety of physical and emotional issues that can rapidly contribute to CRF and reduction in QOL. As a result, the ECOG grade tends to increase as the chemotherapy proceeds. However, the inventors unexpectedly found that the ECOG grades were maintained in all of the studied cases by co-administration of the FIP with chemotherapeutic agents, as shown in Example 5 below.

According to the disclosure provided herein, the term "subject" is intended to encompass human or non-human vertebrates, such as non-human mammal, in need of chemotherapeutic treatment. Non-human mammals include livestock animals, companion animals, laboratory animals, and non-human primates. Non-human subjects also include, without limitation, horses, cows, pigs, goats, dogs, cats, mice, rats, guinea pigs, gerbils, hamsters, mink, rabbits and fish. It is understood that the preferred subject is a human, especially a human patient afflicted with a proliferative disease or at risk for a proliferative disease, such as breast cancer, prostate cancer.

For the purpose of research, the term "subject" may refer to a biological sample as defined herein, which includes but is not limited to a cell, tissue, or organ. Accordingly, the invention disclosed herein is intended to be applied in vivo as well as in vitro.

According to the disclosure provided herein, the term "administering to a subject" includes dispensing, delivering or applying the FIP or the chemotherapeutic agent in a suitable pharmaceutical formulation to a subject by any suitable route for delivery of the FIP or the chemotherapeutic agent to the desired location in the subject to contact the FIP or the chemotherapeutic agent with target cells or tissues.

The FIP may be administered to the subject by any suitable route, such as a topical, rectal, enteral or parenteral route, for example, an oral, intravenous, subcutaneous, intratumoral, intramuscular, intraperitoneal, transdermal, intrathecal, or intracerebral route. Administration can be either rapid as by injection, or over a period of time as by slow infusion or administration of a slow release formulation.

In one preferred embodiment, the FIP is to be administered orally and prepared in the form of an orally administrable formulation. Such formulation is preferably formulated with a suitable carrier, excipient, lubricant, emulsifying agent, suspending agent, sweetening agent, flavor agent, preserving agent and pressed as tablet or encapsulated as solid capsule or soft capsule. It is also contemplated that such formulation can be designed as following dosage forms, either oral solution, or oral sachet, or oral pellet. Or apart from being administered orally, it is contemplated that such formulations are designed as enema, or suppository, or implant, or patch, or cream, or ointment dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulation can additionally include lubricating agents, wetting agents, emulsifying and suspending agents, preserving agents, sweetening agents or flavoring agents. The FIP composition may be formulated so as to provide rapid, sustained, or delayed release of the active ingredients after administration to the patient by employing procedures well known in the art. The formulation can also contain substances that diminish proteolytic, nucleic acid and other degradation and/or substances that promote absorption such as, for example, surface active agents. The composition may be complexed with polyethylene glycol (i.e., PEGylated), albumin or the like to help promote stability in the bloodstream.

In some preferred embodiments, the FIP is formulated into an oral administrable dosage form.

Another preferred preparation for the FIP utilizes a vehicle of physiological saline solution; it is contemplated that other pharmaceutically acceptable carriers such as physiological concentrations of other non-toxic salts or compounds, 5% aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

The FIP may conveniently be formulated in unit dosage form described above by conventional pharmaceutical techniques. Such techniques include the step of bringing into association the FIP and the physiologically acceptable carriers, diluents, adjuvants and/or excipient(s). In general, the formulations are prepared by uniformly and intimately bringing into association the FIP with liquid carriers or finely divided solid carriers or both, and then, if necessary, shaping the product.

The FIP is administered to the subject in a therapeutically effective amount sufficient to ameliorate the adverse side effect caused by a chemotherapeutic agent. The actual dose may be calculated dependent upon the particular route of administration selected. Further refinement of the calculations necessary to determine the appropriate dosage for administration is routinely made by those of ordinary skill in the art. Thus, when administered to a human subject, the FIP is preferably administered daily, weekly or twice a week, at an amount ranging from 0.01 mg/kg body weight/day to 100 mg/kg body weight/day, more preferably from 0.1 mg/kg/day to 10 mg/kg/day. Dose administration can be repeated depending upon the pharmacokinetic parameters of the dosage formulation and the route of administration used.

The chemotherapeutic agent may be administered through various ways, including by parenteral and enteral route systemic administration, in an amount prescribed by qualified personnel.

The FIP and the chemotherapeutic agent may be physically sufficiently distinct for being separately or sequentially administrable. Alternatively, when the FIP and the chemotherapeutic agent are intended for simultaneous use, they can either be physically distinct or be in intimate contact or association. In the latter case, they may for example be mixed together, and/or directly or indirectly complexed onto each other, and/or directly or indirectly linked to each other (e.g., by covalent linkage). For example, they may be formulated into a mixture, complex or linked product is herein encompassed by the application.

Therefore, the term "combination" as used herein refers to an assemblage of agents for use in therapy either by simultaneous, contemporaneous or sequential administration. Simultaneous administration refers to administration of an admixture (whether a true mixture, a suspension, an emulsion or other physical combination) of the FIP and the chemotherapeutic agent. In this case, the combination may be the admixture or separate containers of the FIP and the chemotherapeutic agent that are combined just prior to administration. Contemporaneous administration refers to separate administration of the FIP and the chemotherapeutic agent at the same time, or at times sufficiently close together that an enhanced or synergistic activity relative to the activity of either the agent alone is observed. In this case, the combination comprises separate containers of the FIP and the chemotherapeutic agent.

The following examples are given for the purpose of illustration only and are not intended to limit the scope of the invention.

Example 1: Mice Model

Male BALB/cByJNarl mice (6-8 weeks old) were purchased from National Laboratory Animal Center (NLAC) in Taiwan and randomly divided into four groups, with five mice in Groups Docetaxel+PBS, Docetaxel+FIP-fve and Docetaxel+FIP-gts each and four in Control group. The mice were housed under pathogen-free conditions with a 12-hour light/12-hour dark schedule, and fed an autoclaved diet with ad libitum access to standard rodent chow (Laboratory Rodent Diet 5001, LabDiet, St. Louis, Mo., USA). Three days before the administration of Docetaxel (namely, Day-3), the mice in the Docetaxel+PBS Group started to be fed phosphate-buffered saline (PBS) at 100 μL/animal/day, and the daily feeding of PBS continued throughout the experiment. The mice were injected intravenously in the tail vein with Taxotere® (Aventis Pharma Ltd., Dagenham, UK) at a dose of 30 mg/kg body weight on Days 1, 8 and 15. The Docetaxel+FIP-fve and Docetaxel+FIP-gts Groups were administered Taxotere® at the same dose on the same days as described above. Additionally, the two treatment groups daily received 100 μL PBS added with either 200 μg FIP-fve or 400 μg FIP-gts throughout the experiment starting from Day-3 until the end of the experiment (Day 18). The FIP-gts protein used in this and other Examples disclosed herein was produced according to the method disclosed in WO2005040375A1. The FIP-fve protein used herein was purified from *F. velutipes* by the method disclosed in Ko J. L., *Eur. J. Biochem.* 1995; 228:244-249. The mice of the Control Group were given with PBS alone at 100 μL/animal/day without being injected with anti-cancer agent. Blood was sampled from the orbital sinus of the mice on days 4, 11 and 18 for subsequent analysis. The animals were sacrificed by $CO_2$ asphyxiation on day 18. The protocol of the experiment is illustrated in FIG. 1.

Example 2: Blood Analysis

After sacrifice, whole blood samples obtained from Example 1 were collected from the inferior vena cava of the mice for complete blood counts (CBC). The results are shown in Table I below.

TABLE I

Complete Blood Count Analysis

| | | control | Docetaxel + PBS | Docetaxel + FIP-fve 200 μg/100 μL | Docetaxel + FIP-gts 400 μg/100 μL |
|---|---|---|---|---|---|
| WBC | $(\times 10^3/\mu L)$ | 6.06 ± 1.53 | 3.29 ± 0.80 | 3.72 ± 0.99 | 6.17 ± 1.65 |
| RBC | $(\times 10^6/\mu L)$ | 8.92 ± 0.52 | 7.86 ± 0.24 | 8.31 ± 0.50 | 8.13 ± 0.60 |
| HGB | (g/dL) | 13.38 ± 0.93 | 11.77 ± 0.31 | 12.73 ± 0.39 | 12.08 ± 1.03 |
| HCT | (%) | 45.65 ± 2.19 | 39.94 ± 1.19 | 42.49 ± 2.25 | 40.90 ± 3.59 |
| MCV | (fL) | 51.23 ± 0.07 | 50.82 ± 0.49 | 51.05 ± 0.74 | 50.52 ± 1.35 |
| MCH | (pg) | 15.01 ± 0.21 | 15.00 ± 0.16 | 15.00 ± 0.90 | 14.90 ± 0.60 |
| MCHC | (g/dL) | 29.32 ± 0.41 | 29.48 ± 0.05 | 29.36 ± 1.66 | 29.52 ± 0.36 |
| PLT | $(10^3/\mu L)$ | 435.75 ± 85.46 | 317.88 ± 60.27 | 538.30 ± 62.20 | 359.80 ± 141.83 |
| RDW | (fL) | 29.12 ± 0.28 | 29.26 ± 0.73 | 29.92 ± 0.65 | 30.01 ± 1.43 |
| MPV | (fL) | 6.44 ± 0.15 | 6.71 ± 0.17 | 6.79 ± 0.22 | 6.62 ± 0.27 |

As predicted, the administration with Docetaxel alone led to a considerable reduction in the levels of white blood cells (WBC), red blood cells (RBC), hemoglobin (HGB), hematocrit (HCT) and platelets (PLT) in the mice of the Docetaxel+PBS Group, as compared with the levels in the Control group. However, it was unexpectedly found that the administration of FIP-fve lessened the reduction of both HGB and PLT levels caused by Docetaxel, whereas the co-treatment of FIP-gts with Docetaxel remarkably restored the WBC level to its control value.

Example 3: Structural Integrity of Villus

Figure 2A:
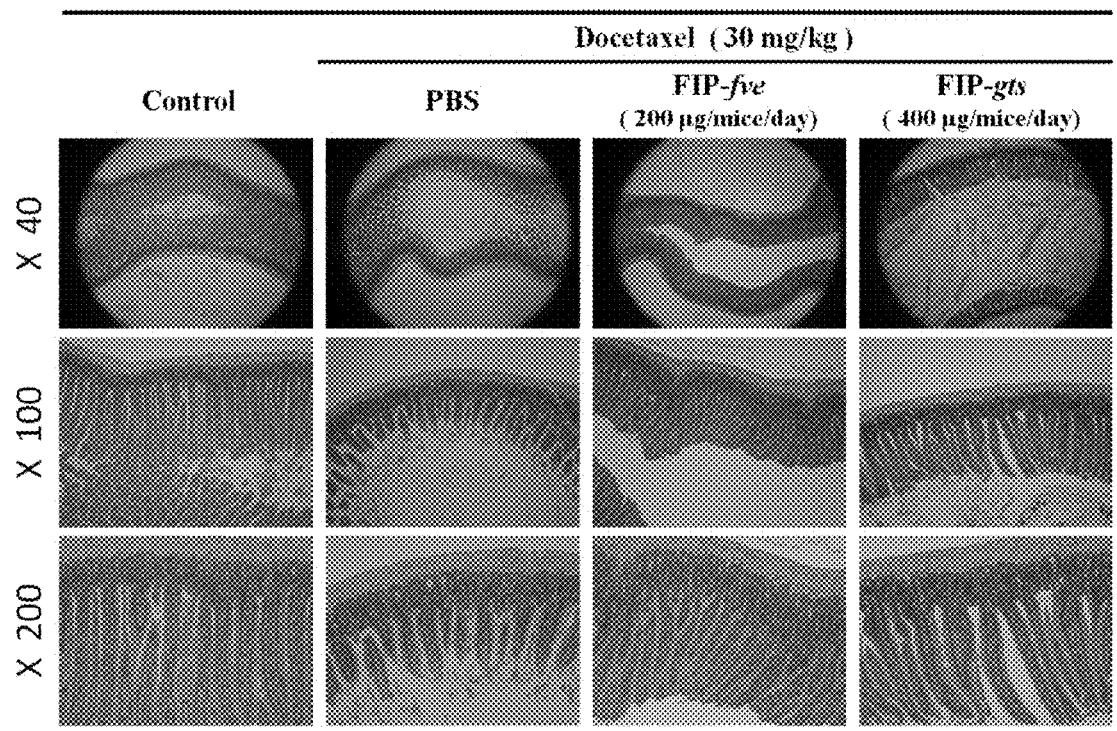
FIG. 2A shows histological images of villi by hematoxylin and eosin staining, showing the morphology of mice villi after administration of PBS, FIP-fve or FIP-gts, followed by co-administration with Docetaxel.
Figure 2B:
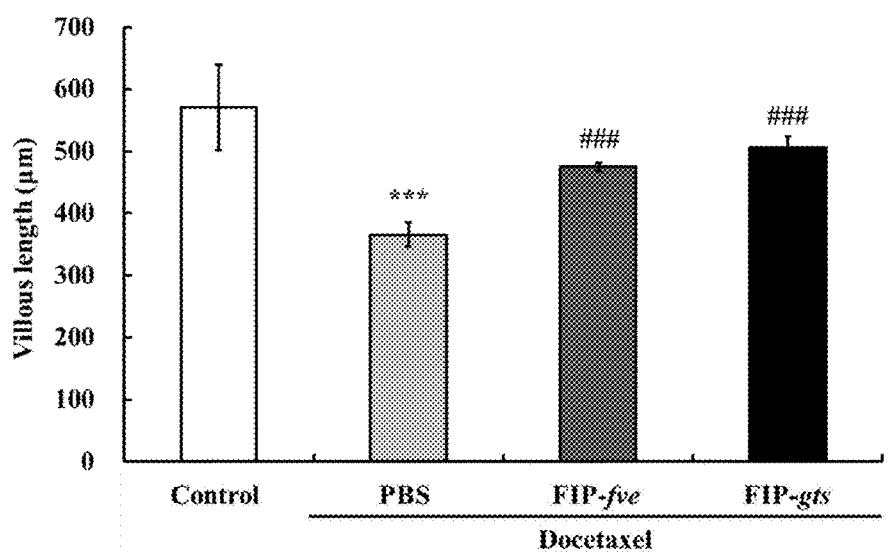
FIG. 2B shows the quantitative analysis of villus length in FIP-fve and FIP-gts treated mice after intravenous injection of Docetaxel, in which the symbol *** indicates P<0.001 versus the Control Group, whereas the symbol ### indicates P<0.001 compared with the group treated with docetaxel alone, and the data were presented as means±SD.

Intestinal samples from the jejunum of the sacrificed mice were fixed in 10% formalin and embedded in paraffin wax. Deparaffinized sections were stained with hematoxylin and eosin using Leica Autostainer XL ST5010 (Leica Microsystems Nussloch GmbH) and then observed under microscope. The histological images of villi appeared in the intestinal samples are shown in FIG. 2A, and the lengths of villi measured by an NIS-Elements D 3.2 image analysis system (Nikon, Japan) were shown in FIG. 2B. These results showed that the villi were severely damaged and blunted in the Docetaxel+PBS Group, evidencing the toxicity of the chemotherapeutic agent to gastric intestinal mucosa. In contrast, the structural integrity of villi was maintained in the samples from the Docetaxel+FIP-fve and Docetaxel+FIP-gts Groups, indicating that the FIPs protected the intestinal mucosa from damage caused by the administration of Docetaxel or even possibly governed or promoted its recovery from the damage.

Example 4: Bone Analysis

Tibiae were separated from right hind limbs of the mice and defleshed. Afterwards, individual tibiae were placed into 15 mL Falcons conical centrifuge tubes (Becton, Dickinson and Company, Franklin Lakes, N.J., USA) and covered with 70% ethanol. The tibia samples were sent to the Taiwan Mouse Clinic, funded by the National Research Program for Biopharmaceuticals (NRPB) of the National Science Council (NSC) in Taiwan, where the samples were scanned by applying three-dimensional micro-computed tomography (micro CT) in a high-resolution low-dose X-ray scanner (SkyScan 1076, Aartselaar, Belgium) and assessed for trabecular bone micro-architecture. For histological analysis, some tibia samples were demineralized in 10% EDTA for two weeks, dehydrated in graded ethanol solutions and embedded in paraffin wax using a Leica ASP300S tissue processor (Leica Microsystems Nussloch GmbH). Deparaffinized sections were stained with hematoxylin and eosin (H&E staining) and then observed under microscope.

Figure 3A:
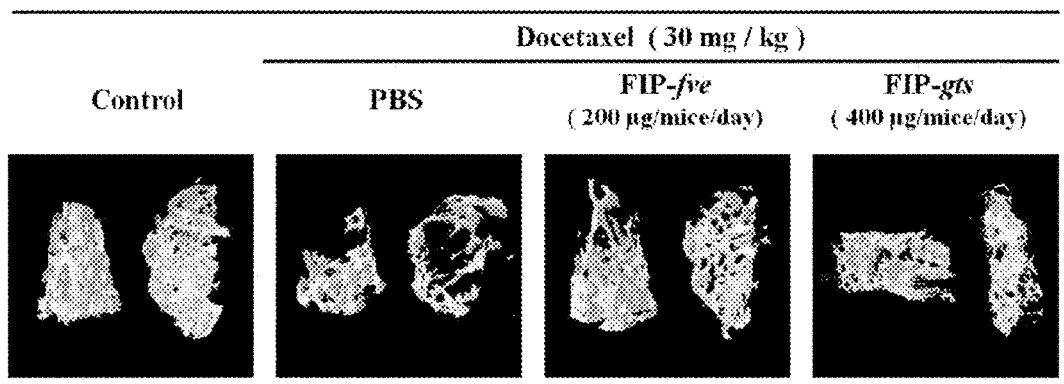
FIGS. 3A-3C show the micro-CT 3D images of the tibia samples from the Control, Docetaxel, Docetaxel+FIP-fve and Docetaxel+FIP-gts Groups.
Figure 3B:
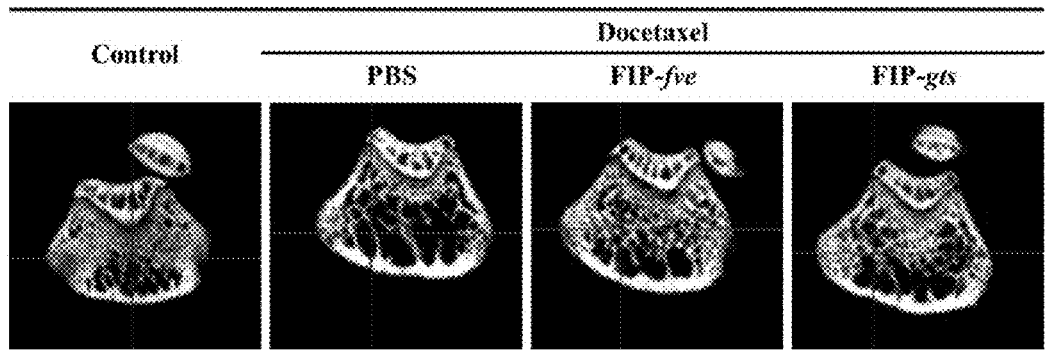
Figure 3C:
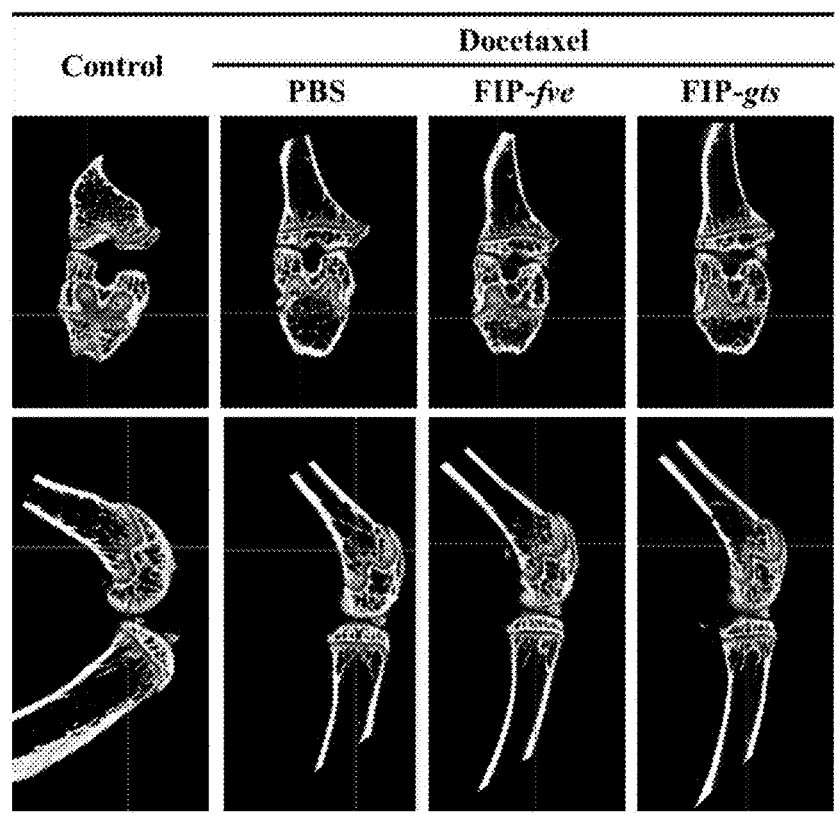

The results of micro CT scanning were shown in FIG. 3A, which indicated that the tibia sample from the Docetaxel+PBS Group is much more osteo-porous than the Control. In contrast, the structural integrity of the tibia was generally maintained in both of the Docetaxel+FIP-fve and Docetaxel+FIP-gts Groups, as compared to that of the Control Group. Similar results were observed in the cross-section view of the knee samples (FIG. 3B) and the longitudinal section view of the distal femur and proximal tibia samples (FIG. 3C), where the samples from the FIP-fve and FIP-gts treated mice groups were shown to be considerably less porous than those from the mice group injected with Docetaxel alone.

The quantitative data in Table II below showed that the mice in the Docetaxel+PBS Group demonstrated a considerable decrease in trabecular bone number (Tb.N) and percent bone volume and an increase in trabecular separation (Tb.Sp) compared to the Control group, evidencing the induction of osteoporosis by Docetaxel treatment. In the tibia samples from the Docetaxel+FIP-fve and Docetaxel+FIP-gts Groups, however, an increase in trabecular bone number and percent bone volume and a significant decline in trabecular separation were observed, suggesting that the symptoms of Docetaxel-induced osteoporosis were alleviated or the development of Docetaxel-induced osteoporosis was prevented by administration of the FIPs. Moreover, trabecular thickness was also found much higher in the Docetaxel+FIP-gts Group than in the other Groups.

TABLE II

| | Quantification of Trabecular Bone | | | | | |
|---|---|---|---|---|---|---|
| | Percent bone volume BV/TV % | Trabecular thickness Tb.Th U | Trabecular separation Tb.Sp U | Trabecular number Tb.N 1/U | Structure model index SMI | Bone surface density BS/TV 1/U |
| Control | 18.9483 | 0.06621 | 0.21191 | 2.86198 | 1.7191 | 11.4475 |
| Doc. + PBS | 5.63389 | 0.06577 | 0.56227 | 0.85661 | 2.1757 | 3.85218 |
| Doc. + FIP-fve | 11.7697 | 0.06629 | 0.31061 | 1.77543 | 2.01096 | 7.52078 |
| Doc. + FIP-gts | 14.5567 | 0.09583 | 0.3659 | 1.51899 | 2.28391 | 6.65796 |

Figure 4A:
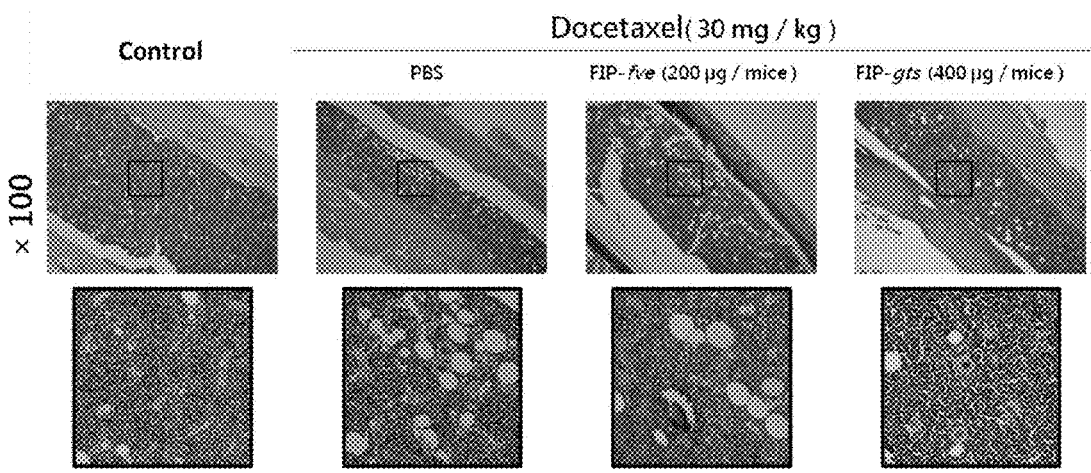
FIG. 4A shows the effects of Docetaxel on bone marrow adipogenesis in vivo, and the effects of FIP-fve and FIP-gts on prevention of adipogenesis.
Figure 4B:
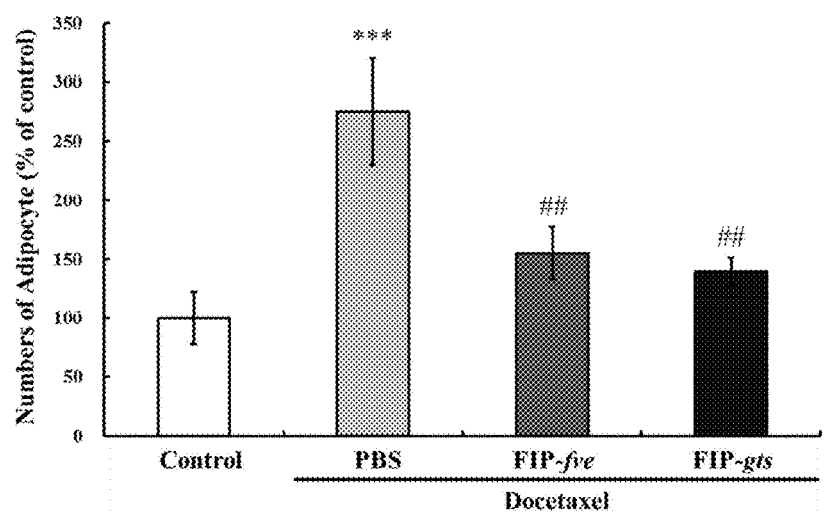
FIG. 4B shows the numbers of adipocyte cells counted under a dissecting microscope, in which the symbol *** indicates P<0.001 versus the Control Group, whereas the symbol ## indicates P<0.01 compared with the group treated with docetaxel alone, and the data presented were as means±SD.

The microscopy images of FIG. 4A, particularly the high magnification images in lower panels, as well as the adipocyte counts demonstrated in FIG. 4B, showed that compared to the Control, there was an increase in marrow adipose tissue accompanied with an decrease in bone volume in the Docetaxel+PBS Group, whereas the Docetaxel+FIP-fve Group and the Docetaxel+FIP-gts Group both demonstrated a relatively moderate level of adipogenesis in tibia bone marrow, indicating a lower severity of osteoporosis.

Example 5: Clinical Studies

Five human patients with stage III or IV lung cancer were enrolled in this study. During the study, each patient was administered Taxotere® at either a low dose of 20-30 mg/m$^2$ or a high dose of 60-69 mg/m$^2$ in conjunction with cisplatin/carboplatin on the designated days as prescribed by the physician, and received daily two tablets of FIP-gts (3 mg/tablet). The patients were asked to come back to the hospital on the designated days for follow up at the clinic and collection of blood samples. The patients were assessed for quality of life and fatigue according to the ECOG performance status system described above. The medical records of the five patients, as well as the administration regimens for the patients, were illustrated in Tables III.A-III.E below.

TABLE III.A

Patient Case 1
Name: Li, x
Year of Birth: 1954 Sex: M
Diagnosis: Lung cancer, right middle lobe, moderately differentiated adenocarcinoma,
cT2N2M1a Stage IV with pleural metastasis and malignant pleural effusion

| Course/Date | C1 2012 Oct. 31 | C2 2012 Nov. 21 | C3 2012 Dec. 13 | C4 2013 Jan. 4 |
|---|---|---|---|---|
| Body height (cm)/Body weight (Kg) | 161/59.4 | 161/61 | 158/62 | 159/63.8 |
| BSA | 1.67 | 1.67 | 1.67 | 1.67 |
| Taxotere ® (mg/m$^2$) | 60 | 60 | 60 | 60 |
| Ciplatin (mg/m$^2$) | 75 | 75 | 75 | 75 |
| Carboplatin (mg) | | | | |

| Course | D-4 | D8 | D15 | D0 | D8 | D16 | D1 | D14 | D1 | D7 | D13 |
|---|---|---|---|---|---|---|---|---|---|---|---|
| Course/Date | 2012 Oct. 26 | 2012 Nov. 27 | 2012 Nov. 14 | 2012 Nov. 20 | 2012 Nov. 28 | 2012 Dec. 6 | 2012 Dec. 13 | 2012 Dec. 26 | 2013 Jan. 4 | 2013 Jan. 10 | 2013 Jan. 16 |
| Nausea | | | | | | | | G1 | | G2 | |
| Vomiting | | | | | | | | | | | |
| Diarrhea | | | | | | | | | | | |
| Stomatitis | | | | | | | | | | | |
| Neuropathy | | | | | | | | | | | |
| Skin rash | | | | | | | | | | | |
| Neutropenia | | | | | | | | | | | |
| Asthenia | | | | | | | | | | | |
| Other | | | | | | | | | | | |
| WBC | 10770 | 5500 | 4650 | 8720 | 6310 | 7100 | 9640 | 6110 | 7030 | | 4160 |
| Seg + band (%) | 71.1 | 75.4 | 44 | 70.9 | 73.7 | 55 | 70 | 73.6 | 66.4 | | 52.5 |
| ANC | 7657 | 4147 | 2046 | 6182 | 4650 | 3905 | 6748 | 4496 | 4667 | | 2184 |
| Hb | 15.1 | 13.5 | | 11.6 | 13 | 12 | 11 | 10.7 | 10.7 | | 10.1 |
| PLT (×10$^{-3}$/μl) | 416 | 234 | | 358 | 207 | 282 | 260 | 190 | 308 | | 274 |
| AST | 20 | | | 16 | | 22 | 16 | | 20 | | |
| ALT | 20 | | | 14 | | 14 | 14 | | 18 | | |
| Cr. | 0.76 | | | 1.53 | | 1.21 | 1.08 | | 1.38 | | |
| CEA/CA125 | 1.288/14.7 | | | | | | | | | | |
| ECOG | 1 | 1 | 1 | 1 | 1 | 1 | 1 | 1 | 1 | | 1 |

| Course/Date | C5 2013 Jan. 25 | C6 2013 Feb. 22 | C7 2013 Mar. 15 | C8 2013 Apr. 12 |
|---|---|---|---|---|
| Body height (cm)/Body weight (Kg) | 158/64.7 | 158/62 | 158/62 | 158/62 |
| BSA | 1.69 | 1.65 | 1.65 | 1.65 |
| Taxotere ® (mg/m$^2$) | 60 | 67 | 67 | 60 |
| Ciplatin (mg/m$^2$) | 66 | | | |
| Carboplatin (mg) | | 450 | 450 | 450 |

| Course | D1 | D8 | D1 | D7 | D1 | D12 | D15 | D1 | D15 |
|---|---|---|---|---|---|---|---|---|---|
| Course/Date | 2013 Jan. 25 | 2013 Feb. 1 | 2013 Feb. 22 | 2013 Feb. 28 | 2013 Mar. 15 | 2013 Mar. 26 | 2013 Mar. 29 | 2013 Apr. 12 | 2013 Apr. 26 |
| Nausea | | G2 | | | | | | | |
| Vomiting | | | | | | | | | |
| Diarrhea | | | | | | | | | |
| Stomatitis | | | | | | | | | |
| Neuropathy | | | | | | | | | |
| Skin rash | | | | | | | | | |
| Neutropenia | | | | | | G3 | G3 | | G3 |
| Asthenia | | G2 | | G2 | G1 | G1 | G1 | | |
| Other | | | | | | | | | |
| WBC | 9560 | 4510 | 7650 | 4110 | 8020 | 2360 | 3140 | 7650 | 2620 |
| Seg + band (%) | 70 | 74 | 77.2 | 64.9 | 72.8 | 23.3 | 25 | 73.3 | 34.3 |
| ANC | 6692 | 3337 | 5905 | 2667 | 5938 | 549 | 785 | 5607 | 898 |
| Hb | 9.6 | 8.8 | 9.2 | 8.7 | 10.2 | 9 | 11 | 10.3 | |
| PLT (×10$^{-3}$/μl) | 312 | | 246 | 208 | 141 | 136 | 133 | 191 | |

TABLE III.A-continued

Patient Case 1
Name: Li, x
Year of Birth: 1954 Sex: M
Diagnosis: Lung cancer, right middle lobe, moderately differentiated adenocarcinoma,
cT2N2M1a Stage IV with pleural metastasis and malignant pleural effusion

| | | | | | | | | | | |
|---|---|---|---|---|---|---|---|---|---|---|
| AST | 21 | | 20 | | 18 | | 18 | | | |
| ALT | 16 | | 15 | | 14 | | 17 | | | |
| Cr. | 1.56 | | 1.52 | | 1.51 | | 1.17 | | | |
| CEA/CA125 | 1.452/ 7.01 | | 1.417/ 6.58 | | | | 1.086/ 5.70 | | | |
| ECOG | 1 | 1 | 1 | 1 | 1 | 1 | 1 | 1 | 1 | 1 |

| Course/Date | C9 2013 May 10 | | C10 2013 Jun. 7 | | C11 2013 Jul. 5 | | C12 2013 Aug. 2 | |
|---|---|---|---|---|---|---|---|---|
| Body height (cm)/Body weight (Kg) | 158/62 | | 158/62 | | 158/62 | | 158/62 | |
| BSA | 1.65 | | 1.65 | | 1.65 | | 1.65 | |
| Taxotere ® (mg/m$^2$) | 60 | | 60 | | 60 | | 60 | |
| Ciplatin (mg/m$^2$) | | | | | | | | |
| Carboplatin (mg) | | | | | | | | |

| Course Course/Date | D1 2013 Apr. 12 | D8 2013 Apr. 26 | D1 2013 Jun. 7 | D15 2013 Jun. 21 | D1 2013 Jul. 5 | D15 2013 Jul. 19 | D1 2013 Aug. 2 |
|---|---|---|---|---|---|---|---|
| Nausea | | | | | | | |
| Vomiting | | | | | | | |
| Diarrhea | | | | | | | |
| Stomatitis | | | | | | | |
| Neuropathy | G1 | G1 | G1 | G1 | G1 | G1 | G1 |
| Skin rash | | | | | | | |
| Neutropenia | | | | | | | |
| Asthenia | | | | | | | |
| Other | | | | | | | |
| WBC | 6070 | 3920 | 9280 | 5700 | 8010 | 4810 | 9160 |
| Seg + band (%) | 68.7 | 61.7 | 73.9 | 69 | 70.6 | 55 | 73.9 |
| ANC | 4170 | 2418 | 6857 | 3933 | 5655 | 2645 | 6769 |
| Hb | 9.7 | | 9.6 | | 10.4 | | 10.8 |
| PLT (×10$^{-3}$/μl) | 254 | | 302 | | 299 | | 248 |
| AST | 19 | | 18 | | | | 20 |
| ALT | 18 | | 18 | | | | 22 |
| Cr. | 1.33 | | 1.37 | | | | 1.55 |
| CEA/CA125 | | | | | | | |
| ECOG | 1 | 1 | 1 | 1 | 1 | 1 | 1 |

TABLE III.B

Patient Case 2
Name: Lu, x
Year of Birth: 1952 Sex: M
Diagnosis: Adenocarcinoma of lung (EGFR mutation WT), moderately
differentiated, left upper lobe, with T3,4 spine metastasis, cT4N3M1b, stage IV

| Course/Date | C1 2013 Jan. 30 | C2 2013 Feb. 21 | C3 2013 Mar. 20 |
|---|---|---|---|
| Body height (cm)/Body weight (Kg) | 162/72.8 | 167/73.4 | 163/72 |
| BSA | 1.82 | 1.83 | 1.81 |
| Taxotere ® (mg/m$^2$) | 66 | 60 | 55 |
| Ciplatin (mg/m$^2$) | 75 | 75 | |
| Carboplatin (mg) | | | 600 |

| Course Course/Date | D1 2013 Jan. 30 | D8 2013 Feb. 6 | D10 2013 Feb. 8 | D0 2013 Feb. 20 | D7 2013 Feb. 27 | D16 2013 Mar. 8 | D21 2013 Mar. 13 | D1 2013 Mar. 20 | D8 2013 Mar. 27 |
|---|---|---|---|---|---|---|---|---|---|
| Nausea | | | | G2 | G1 | | | | |
| Vomiting | | G3 | | G1 | G1 | | | | G1 |
| Diarrhea | | G2 | | | | | | | |

TABLE III.B-continued

Patient Case 2
Name: Lu, x
Year of Birth: 1952 Sex: M
Diagnosis: Adenocarcinoma of lung (EGFR mutation WT), moderately
differentiated, left upper lobe, with T3,4 spine metastasis, cT4N3M1b, stage IV

|  |  |  |  |  |  |  |  |  |
|---|---|---|---|---|---|---|---|---|
| Stomatitis |  |  |  | G2 |  |  |  |  |
| Neuropathy |  |  |  |  |  |  |  |  |
| Skin rash |  |  |  |  |  |  |  |  |
| Neutropenia |  | G4 |  | G2 |  | G1 |  |  |
| Asthenia |  |  |  |  |  |  |  |  |
| Other |  |  |  |  |  |  |  |  |
| WBC | 8810 | 970 |  | 5210 | 1410 | 3220 | 5510 | 4360 |
| Seg + band (%) | 87.4 | 23 |  | 75.6 | 71 | 61.9 | 69.1 | 73.6 |
| ANC | 7699 | 223.1 |  | 3938 | 1001 | 1993 | 3807 | 3208 |
| Hb | 12.2 | 12 |  | 9.6 | 9.9 | 10.3 |  |  |
| PLT (×10$^{-3}$/μl) | 279 |  |  | 248 |  | 193 |  |  |
| AST | 11 |  |  | 18 |  |  |  |  |
| ALT | 11 |  |  | 18 |  |  |  |  |
| Cr. | 1.25 |  |  | 1.37 |  |  |  |  |
| CEA/CA125 | X/63.1 |  |  |  |  | 2.772/39.7 |  |  |
| ECOG | 1 | 1 | 1 | 1 | 1 | 1 | 1 | 1 |

| Course/ | C4 | C5 | C6 |
|---|---|---|---|
| Date | 2013 Apr. 10 | 2013 May 2 | 2013 May 22 |
| Body height (cm)/Body weight (Kg) | 163/73 | 163/73 | 163/73 |
| BSA | 1.82 | 1.82 | 1.82 |
| Taxotere ® (mg/m$^2$) | 55 | 55 | 55 |
| Ciplatin (mg/m$^2$) |  |  |  |
| Carboplatin (mg) | 450 | 450 | 450 |

| Course | D1 | D8 | D15 | D0 | D7 | D14 | D1 | D8 | D22 |
|---|---|---|---|---|---|---|---|---|---|
| Course/Date | 2013 Apr. 10 | 2013 Apr. 17 | 2013 Apr. 24 | 2013 May 1 | 2013 May 8 | 2013 May 15 | 2013 May 22 | 2013 May 29 | 2013 Jun. 12 |
| Nausea |  |  |  |  |  |  |  |  |  |
| Vomiting |  |  |  |  |  |  |  |  |  |
| Diarrhea |  |  |  |  |  |  |  |  |  |
| Stomatitis |  |  |  |  |  |  |  |  |  |
| Neuropathy |  |  |  | G1 | G1 | G1 | G1 | G1 | G1 |
| Skin rash |  |  |  |  |  |  |  |  |  |
| Neutropenia |  | G3 |  |  | G2 |  |  | G1 |  |
| Asthenia |  | G1 |  |  |  |  |  |  |  |
| Other |  |  |  |  |  |  |  |  |  |
| WBC | 4920 | 1490 |  | 6020 | 2000 |  | 7830 | 2610 | 3200 |
| Seg + band (%) | 70 | 55 |  | 80.4 | 60.5 |  | 78 | 60.1 | 66.3 |
| ANC | 3444 | 819.5 |  | 4840 | 1210 |  | 6107 | 1568 | 2121 |
| Hb | 12.3 |  |  | 11.1 |  |  | 9.9 |  | 9.2 |
| PLT (×10$^{-3}$/μl) | 105 |  |  | 148 |  |  | 135 |  | 110 |
| AST | 20 |  |  | 16 |  |  | 16 |  |  |
| ALT | 22 |  |  | 12 |  |  | 12 |  |  |
| Cr. | 1.55 |  |  | 1.08 |  |  | 1.68 |  |  |
| CEA/CA125 |  |  |  | 3.762/66.5 |  |  | 2.510/66.9 |  | 2.545/54.4 |
| ECOG | 1 | 1 | 1 | 1 | 1 | 1 | 1 | 1 | 1 |

TABLE III.C

Patient Case 3
Name: Tsai, x
Year of Birth: 1949 Sex: M
Diagnosis: Squamous cell carcinoma of lung,
left upper lobe, cT2bN3M0 stage IIIB

| Course/date | C1 2013 Apr. 19 | C2 2013 May 10 | C3 2013 May 31 |
|---|---|---|---|
| Body height (cm)/Body weight (Kg) | 158/71 | 156/71 | 156/71 |
| BSA | 1.75 | 1.75 | 1.75 |
| Taxotere ® (mg/m$^2$) | 62 | 63 | 63 |
| Ciplatin (mg/m$^2$) | 75 | 75 | 75 |
| Carboplatin (mg) |  |  |  |

TABLE III.C-continued

Patient Case 3
Name: Tsai, x
Year of Birth: 1949 Sex: M
Diagnosis: Squamous cell carcinoma of lung,
left upper lobe, cT2bN3M0 stage IIIB

| Course | D1 | D8 | D1 | D8 | D1 | D8 | D22 |
|---|---|---|---|---|---|---|---|
| Course/ | 2013 | 2013 | 2013 | 2013 | 2013 | 2013 | 2013 |
| Date | Apr. 19 | Apr. 26 | May 10 | May 17 | May 31 | Jun. 7 | Jun. 21 |
| Nausea | | | | G1 | | | |
| Vomiting | | G1 | | G1 | | | |
| Diarrhea | | | | | | | |
| Stomatitis | | G1 | | G2 | | | |
| Neuropathy | | | | | | | |
| Skin rash | | | | | | | |
| Neutropenia | | G3 | | G2 | | G2 | |
| Asthenia | | | | | | G1 | |
| Other | | | | | | | |
| WBC | 9420 | 3460 | 11600 | 3100 | 9020 | 3210 | 8550 |
| Seg + band (%) | 71.2 | 24.3 | 63.5 | 41 | 62.2 | 34 | 62.2 |
| ANC | 6707 | 840 | 7366 | 1271 | 5610 | 1091 | 5318 |
| Hb | 14.9 | | 13.9 | | 12 | | 11 |
| PLT (×10$^{-3}$/μl) | 307 | | 258 | | 226 | | 227 |
| AST | 14 | | 13 | | 15 | | 13 |
| ALT | 13 | | 15 | | 12 | | 6 |
| Cr. | 1.09 | | 0.94 | | 0.86 | | 0.99 |
| CEA/CA125 | 2.141/X | | | | | | |
| SCC | 1.8 | | | | | | 3.3 |
| ECOG | 0 | 0 | 0 | 0 | 0 | 0 | 0 |

TABLE III.D

Patient Case 4
Name: Chang, x
Year of Birth: 1966 Sex: M
Diagnosis: Adenocarcinoma of lung (EGFR wild type), left upper lobe with
mediastinal invasion, T4N3M0, stage IIB, disease progression with bone metastasis

| Course/ | C1-1 2013 Apr. 26 | | C2-1 2013 May 17 | | C3-1 2013 Jun. 14 | | C4-1 2013 Jul. 12 | |
| Date | C1-2 2013 May 3 | | C2-2 2013 May 24 | | C3-2 2013 Jun. 28 | | C4-2 2013 Jul. 26 | |
|---|---|---|---|---|---|---|---|---|
| Body height (cm)/Body weight (Kg) | 176/86 | | 176/86 | | 176/86 | | 176/86 | |
| BSA | 2.05 | | 2.05 | | 2.05 | | 2.05 | |
| Taxotere ® (mg/m$^2$) | 29.3 | 29.3 | 29.3 | 29.3 | 29.3 | 29.3 | 29.3 | 20 |
| Ciplatin (mg/m$^2$) | 34 | 41 | 41 | 41 | 41 | 41 | | |
| Carboplatin (mg) | | | | | | | 600 | |

| Course | D1 | D8 | D1 | D8 | D16 | D1 | D15 | D1 | D15 |
| Course/ | 2013 | 2013 | 2013 | 2013 | 2013 | 2013 | 2013 | 2013 | 2013 |
| Date | Apr. 26 | May 3 | May 17 | May 24 | Jun. 7 | Jun. 14 | Jun. 28 | Jul. 12 | Jul. 26 |
|---|---|---|---|---|---|---|---|---|---|
| Nausea | | | | | | | | | |
| Vomiting | | | | | | | | | |
| Diarrhea | | | | | | | | | |
| Stomatitis | | | | | | | | | |
| Neuropathy | | | | | G1 | G1 | G1 | G1 | G1 |
| Skin rash | | | | | | | | | |
| Neutropenia | | | | | | | | | |
| Asthenia | | G1 | G1 | G1 | | | | | |
| Other | | | | | | | | | |
| WBC | 4580 | 6070 | 4280 | 4150 | 2430 | 4050 | 4220 | 4100 | 3210 |
| Seg + band (%) | 46.3 | 68.8 | 59.2 | 57.7 | 40 | 41.5 | 54.6 | 61.5 | 48 |
| ANC | 2120 | 4176 | 2533 | 2394 | 972 | 1680 | 2304 | 2521 | 1540 |
| Hb | 11.2 | 11.2 | 10 | | 8.6 | | 9.5 | 9.6 | 8.9 |
| PLT (×10$^{-3}$/μl) | 207 | 181 | 143 | | 179 | | 191 | 142 | 78 |
| AST | 18 | | 13 | | | | 15 | | |
| ALT | 10 | | 10 | | | | 9 | | |
| Cr. | 0.8 | | 0.89 | | | | 1.15 | | |

TABLE III.D-continued

Patient Case 4
Name: Chang, x
Year of Birth: 1966 Sex: M
Diagnosis: Adenocarcinoma of lung (EGFR wild type), left upper lobe with
mediastinal invasion, T4N3M0, stage IIB, disease progression with bone metastasis

| | | | | | | | | | |
|---|---|---|---|---|---|---|---|---|---|
| CEA/CA125 | 9.434/ 19.3 | | 11.335/ 15.7 | | 9.343/ X | | | 9.118/ 10.4 | |
| ECOG | 1 | 1 | 1 | 1 | 1 | 1 | 1 | 1 | 1 |

TABLE III.E

Patient Case 5
Name: Zheng, x
Year of Birth: 1944 Sex: M
Diagnosis: AdenoCa. of RUL, s/p wedge resection and pleural biopsy on 2011 Jul. 28.
Pathology: AdenoCa. (EGFR WT) with pleural metastasis, pT2aNxM1a,
receiving CCRT with Docetaxel and Cisplatin.

| Course/Date | C1-1 2013 Jun. 21 C1-2 2013 Jun. 28 C1-3 2013 Jul. 5 | | | C2-1 2013 Jul. 19 C2-2 2013 Jul. 26 C2-2 2013 Aug. 2 | | |
|---|---|---|---|---|---|---|
| Body height (cm)/Body weight (Kg) | 169/69 | | | 169/69 | | |
| BSA | | 1.8 | | | 1.8 | |
| Taxotere ® (mg/m$^2$) | 20 | 20 | 20 | | | 20 |
| Ciplatin (mg/m$^2$) | 25 | 25 | 25 | 25 | 25 | 25 |
| Carboplatin (mg) | | | | | | |

| Course Course/ Date | D1 2013 May 4 | D8 2013 Jun. 8 | D15 2013 Jul. 5 | D1 2013 Jul. 19 | D8 2013 Jul. 26 | D15 2013 Aug. 2 |
|---|---|---|---|---|---|---|
| Nausea | | | | | | |
| Vomiting | | | | | | |
| Diarrhea | | | | | | |
| Stomatitis | | | G1 | | | |
| Neuropathy | | | | | | |
| Skin rash | | | | | | |
| Neutropenia | | | | G1 | G1 | |
| Asthenia | | | | | | |
| Other | | | | | | |
| WBC | 5340 | 5510 | 4660 | 2970 | 2850 | 4130 |
| Seg + band (%) | | | 64 | 64.7 | 69.1 | 74.9 |
| ANC | | | 2982.4 | 1921.59 | 1969.35 | 3093.37 |
| Hb | 13.2 | 11.9 | | 11.8 | | |
| PLT (×10$^{-3}$/μl) | 145 | 115 | | 123 | | |
| AST | 15 | 15 | | 18 | | |
| ALT | 16 | 20 | | 18 | | |
| Cr. | 0.9 | 1.02 | | 0.83 | | |
| CEA/CA125 | 29.141/10.3 | 34.906/10.8 | | | | |
| ECOG | 0 | 0 | 0 | 0 | 0 | 0 |

As shown in Tables III.A-III.E, the ECOG grades for all of the patients remained unchanged during the entire course of therapy, verifying the effects of the FIP on maintenance of QOL and prevention of CRF.

While the invention has been described with reference to the preferred embodiments above, it should be recognized that the preferred embodiments are given for the purpose of illustration only and are not intended to limit the scope of the present invention and that various modifications and changes, which will be apparent to those skilled in the relevant art, may be made without departing from the spirit and scope of the invention.

All papers, publications, literature, patents, patent applications, websites, and other printed or electronic documents referred herein, including but not limited to the references listed below, are incorporated by reference in their entirety. In case of conflict, the present description, including definitions, will prevail.

We claim:

1. A method for protecting a subject from an adverse side effect caused by a chemotherapeutic agent, comprising administering to said subject an effective amount of at least partially purified fungal immunomodulatory protein (FIP) sufficient to ameliorate the adverse side effect, wherein the adverse side effect is selected from the group consisting of mucositis, osteoporosis, fatigue, diminished quality of life, alopecia and pain, wherein the chemotherapeutic agent is a taxane.

2. The method according to claim 1, wherein the FIP has an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

3. The method according to claim 2, wherein the FIP has the amino acid sequence of SEQ ID NO: 1.

4. The method according to claim 1, wherein the taxane is selected from the group consisting of Paclitaxel and Docetaxel.

5. The method according to claim 1, wherein the adverse side effect is selected from the group consisting of gastro-intestinal mucositis, chemotherapy-induced osteoporosis and cancer-related fatigue.

6. The method according to claim 1, wherein the FIP is in an orally administerable form.

7. The method according to claim 1, wherein the FIP is used at an amount ranging from 0.1 mg/kg body weight/day to 10 mg/kg body weight/day.

8. The method according to claim 1, wherein the subject is selected from the group consisting of human and non-human vertebrates.

9. The method according to claim 1, wherein the protecting is directed to preventing the adverse side effect from occurring.

* * * * *

SEQUENCE LISTING

<160> NUMBER OF SEQ ID NOS: 8

<210> SEQ ID NO 1
<211> LENGTH: 111
<212> TYPE: PRT
<213> ORGANISM: Ganoderma tsugae
<220> FEATURE:
<221> NAME/KEY: PEPTIDE
<222> LOCATION: (1)...(111)

<400> SEQUENCE: 1

Met Ser Asp Thr Ala Leu Ile Phe Arg Leu Ala Trp Asp Val Lys Lys
1               5                   10                  15

Leu Ser Phe Asp Tyr Thr Pro Asn Trp Gly Arg Gly Asn Pro Asn Asn
                20                  25                  30

Phe Ile Asp Thr Val Thr Phe Pro Lys Val Leu Thr Asp Lys Ala Tyr
            35                  40                  45

Thr Tyr Arg Val Ala Val Ser Gly Arg Asn Leu Gly Val Lys Pro Ser
    50                  55                  60

Tyr Ala Val Glu Ser Asp Gly Ser Gln Lys Val Asn Phe Leu Glu Tyr
65                  70                  75                  80

Asn Ser Gly Tyr Gly Ile Ala Asp Thr Asn Thr Ile Gln Val Phe Val
                85                  90                  95

Val Asp Pro Asp Thr Asn Asn Asp Phe Ile Ile Ala Gln Trp Asn
            100                 105                 110

<210> SEQ ID NO 2
<211> LENGTH: 114
<212> TYPE: PRT
<213> ORGANISM: Flammulina Velutipes
<220> FEATURE:
<221> NAME/KEY: PEPTIDE
<222> LOCATION: (1)...(114)

<400> SEQUENCE: 2

Ser Ala Thr Ser Leu Thr Phe Gln Leu Ala Tyr Leu Val Lys Lys Ile
1               5                   10                  15

Asp Phe Asp Tyr Thr Pro Asn Trp Gly Arg Gly Thr Pro Ser Ser Tyr
                20                  25                  30

Ile Asp Asn Leu Thr Phe Pro Lys Val Leu Thr Asp Lys Lys Tyr Ser
            35                  40                  45

Tyr Arg Val Val Val Asn Gly Ser Asp Leu Gly Val Glu Ser Asn Phe
    50                  55                  60

Ala Val Thr Pro Ser Gly Gly Gln Thr Ile Asn Phe Leu Gln Tyr Asn
65                  70                  75                  80

Lys Gly Tyr Gly Val Ala Asp Thr Lys Thr Ile Gln Val Phe Val Val
                85                  90                  95

Ile Pro Asp Thr Gly Asn Ser Glu Glu Tyr Ile Ile Ala Glu Trp Lys
            100                 105                 110

Lys Thr

<210> SEQ ID NO 3
<211> LENGTH: 112
<212> TYPE: PRT
<213> ORGANISM: Volvariella volvacea
<220> FEATURE:
<221> NAME/KEY: PEPTIDE
<222> LOCATION: (1)...(112)

<400> SEQUENCE: 3

```
Ser Thr Asp Leu Thr Gln Leu Leu Phe Phe Ile Ala Tyr Asn Leu Gln
1               5                   10                  15

Lys Val Asn Phe Asp Tyr Thr Pro Gln Trp Gln Arg Gly Asn Pro Ser
            20                  25                  30

Ser Tyr Ile Asp Ala Val Val Phe Pro Arg Val Leu Thr Asn Lys Ala
        35                  40                  45

Tyr Gln Tyr Arg Val Val Thr Gly Asp Lys Asp Leu Gly Ile Lys Pro
    50                  55                  60

Ser Tyr Ser Val Gln Ala Asp Gly Ser Gln Lys Val Asn Leu Leu Glu
65                  70                  75                  80

Tyr Asn Gly Gly Tyr Gly Val Ala Asp Thr Thr Ile Lys Ile Tyr
                85                  90                  95

Val Val Asp Pro Ser Asn Gly Asn Gln Tyr Leu Ile Ala Gln Trp Lys
                100                 105                 110
```

<210> SEQ ID NO 4
<211> LENGTH: 111
<212> TYPE: PRT
<213> ORGANISM: Ganoderma lucidum
<220> FEATURE:
<221> NAME/KEY: PEPTIDE
<222> LOCATION: (1)...(111)

<400> SEQUENCE: 4

```
Met Ser Asp Thr Ala Leu Ile Phe Arg Leu Ala Trp Asp Val Lys Lys
1               5                   10                  15

Leu Ser Phe Asp Tyr Thr Pro Asn Trp Gly Arg Gly Asn Pro Asn Asn
            20                  25                  30

Phe Ile Asp Thr Val Thr Phe Pro Lys Val Leu Thr Asp Lys Ala Tyr
        35                  40                  45

Thr Tyr Arg Val Ala Val Ser Gly Arg Asn Leu Gly Val Lys Pro Ser
    50                  55                  60

Tyr Ala Val Glu Ser Asp Gly Ser Gln Lys Val Asn Phe Leu Glu Tyr
65                  70                  75                  80

Asn Ser Gly Tyr Gly Ile Ala Asp Thr Asn Thr Ile Gln Val Phe Val
                85                  90                  95

Val Asp Pro Asp Thr Asn Asn Asp Phe Ile Ile Ala Gln Trp Asn
                100                 105                 110
```

<210> SEQ ID NO 5
<211> LENGTH: 111
<212> TYPE: PRT
<213> ORGANISM: Ganoderma japoncium
<220> FEATURE:
<221> NAME/KEY: PEPTIDE
<222> LOCATION: (1)...(111)

<400> SEQUENCE: 5

```
Met Ser Asp Thr Ala Leu Ile Phe Arg Leu Ala Trp Asp Val Lys Lys
1               5                   10                  15

Leu Ser Phe Asp Tyr Thr Pro Thr Trp Gly Arg Gly Asn Pro Ser Arg
            20                  25                  30

Phe Val Asp Asn Val Thr Phe Pro Gln Val Leu Ala Asp Lys Ala Tyr
        35                  40                  45

Thr Tyr Arg Val Val Val Ser Gly Arg Asp Leu Gly Val Arg Pro Ser
    50                  55                  60

Tyr Ala Val Gly Ser Asp Gly Ser Gln Lys Val Asn Phe Leu Glu Tyr
65                  70                  75                  80
```

```
Asn Gln Gly Tyr Gly Ile Ala Asp Thr Asn Thr Ile Gln Val Phe Val
                85                  90                  95

Ile Asp Pro Asp Thr Asp Ala Asp Phe Ile Ile Ala Gln Trp Asn
        100                 105                 110
```

<210> SEQ ID NO 6
<211> LENGTH: 111
<212> TYPE: PRT
<213> ORGANISM: Ganoderma microsporum
<220> FEATURE:
<221> NAME/KEY: PEPTIDE
<222> LOCATION: (1)...(111)

<400> SEQUENCE: 6

```
Met Ser Asp Thr Ala Leu Ile Phe Thr Leu Ala Trp Asn Val Lys Gln
1               5                   10                  15

Leu Ala Phe Asp Tyr Thr Pro Asn Trp Gly Arg Gly Arg Pro Ser Ser
                20                  25                  30

Phe Ile Asp Thr Val Thr Phe Pro Thr Val Leu Thr Asp Lys Ala Tyr
            35                  40                  45

Thr Tyr Arg Val Val Val Ser Gly Lys Asp Leu Gly Val Arg Pro Ser
50                  55                  60

Tyr Ala Val Glu Ser Asp Gly Ser Gln Lys Ile Asn Phe Leu Glu Tyr
65                  70                  75                  80

Asn Ser Gly Tyr Gly Ile Ala Asp Thr Asn Thr Ile Gln Val Tyr Val
                85                  90                  95

Ile Asp Pro Asp Thr Gly Asn Asn Phe Ile Val Ala Gln Trp Asn
        100                 105                 110
```

<210> SEQ ID NO 7
<211> LENGTH: 111
<212> TYPE: PRT
<213> ORGANISM: Ganoderma sinense
<220> FEATURE:
<221> NAME/KEY: PEPTIDE
<222> LOCATION: (1)...(111)

<400> SEQUENCE: 7

```
Met Ser Asp Thr Ala Leu Ile Phe Arg Leu Ala Trp Asp Val Lys Lys
1               5                   10                  15

Leu Ser Phe Asp Tyr Thr Pro Thr Trp Gly Arg Gly Asn Pro Ser Arg
                20                  25                  30

Phe Val Asp Asn Val Thr Phe Pro Gln Val Leu Ala Asp Lys Ala Tyr
            35                  40                  45

Thr Tyr Arg Val Val Val Ser Gly Arg Asp Leu Gly Val Arg Pro Ser
        50                  55                  60

Tyr Ala Val Gly Ser Asp Gly Ser Gln Lys Val Asn Phe Leu Glu Tyr
65                  70                  75                  80

Asn Gln Gly Tyr Gly Ile Ala Asp Thr Asn Thr Ile Gln Val Phe Val
                85                  90                  95

Ile Asp Pro Asp Thr Gly Ala Asp Phe Ile Ile Ala Gln Trp Asn
        100                 105                 110
```

<210> SEQ ID NO 8
<211> LENGTH: 114
<212> TYPE: PRT
<213> ORGANISM: Nectria haematococca
<220> FEATURE:
<221> NAME/KEY: PEPTIDE
<222> LOCATION: (1)...(114)

```
<400> SEQUENCE: 8

Met Ala Thr Thr Asn Asp Ser Ala Val Leu Phe Tyr Ile Val Ala Ser
1               5                   10                  15

Gln Lys Lys Leu Ser Phe Asp Tyr Thr Pro Asn Trp Gly Arg Gly Ser
            20                  25                  30

Pro Asn Ser Tyr Ile Asp Asn Leu Thr Phe Pro Arg Val Leu Thr Asn
            35                  40                  45

Lys Pro Tyr Lys Tyr Arg Val Val Lys Ala Gly Gln Asp Leu Gly Val
        50                  55                  60

Arg Asp Ser Tyr Ser Val Gln Ser Asp Gly Ser Gln Lys Val Asn Phe
65                  70                  75                  80

Leu Glu Tyr Asn Ala Gly Arg Gly Ile Ala Asp Thr Gln Thr Ile Gln
                85                  90                  95

Val Tyr Val Val Asp Pro Asp Asn Gly Asn Gln Tyr Leu Val Ala Gln
                100                 105                 110

Trp Lys
```